United States Patent [19]

Gocho

[11] 4,311,667
[45] Jan. 19, 1982

[54] DELIVERING APPARATUS

[75] Inventor: Nagahiro Gocho, Hachioji, Japan

[73] Assignee: Olympus Optical Company Limited, Tokyo, Japan

[21] Appl. No.: 140,567

[22] Filed: Apr. 15, 1980

[30] Foreign Application Priority Data

Apr. 19, 1979 [JP] Japan ................................. 54/48197

[51] Int. Cl.³ .................... G01N 1/14; G01N 35/06
[52] U.S. Cl. ................................... 422/64; 73/864.24; 141/130; 422/65; 422/100
[58] Field of Search ................ 422/63, 64, 65, 67, 422/100; 364/497; 73/425.6, 423 A; 141/130

[56] References Cited

U.S. PATENT DOCUMENTS 3,912,456  10/1975  Young ................................. 422/64
4,058,367  11/1967  Gilford .............................. 422/63

Primary Examiner—Ronald Serwin

[57] ABSTRACT

An apparatus comprising a delivering device including a probe and operative to suck at least one kind of liquids such as a plurality of reagents, samples or the like from respective vessels into the probe and deliver the liquid thus sucked from the probe into a reaction vessel. In such kind of delivering apparatus, provision is made of the improvement in which the probe is movable along a given moving path, the vessels containing the liquids to be delivered being provided with suction openings arranged at a plurality of fixed positions along the moving path of the probe, and in which the reaction vessel is movable along a path adjacent to and crossed with the moving path of the probe, and in which provision is made of means for locating the probe at any sucking position or at a delivering position with respect to the reaction vessel where the moving path of the probe is adjacent to or crossed with the moving path of the reaction vessel.

8 Claims, 7 Drawing Figures

DELIVERING APPARATUS

BACKGROUND OF THE INVENTION

1. Field of the Invention

The present invention relates to an apparatus comprising at least one delivering device which can suck one or more kinds of liquids such as a plurality of reagents, samples or the like from respective vessels into respective probes and which can deliver the sucked liquids from the probes into reaction vessels.

2. Description of the Prior Art

The above described kind of delivering apparatus is used for an automatic chemical analytical apparatus or the like dealing with a much amount of samples and is intended to deliver reagents corresponding to respective samples and test informations (analytical items) into reaction vessels. In such kind of delivering apparatus, contamination of the samples and reagents must be eliminated as much as possible in order to prevent degradation of the accuracy in analysis.

As one of the solutions for the above mentioned problem, it has been proposed to provide a plurality of delivering apparatus corresponding to each reagent. Such construction, however, is very inconvenient in space and cost. As another solution, it has been well known to provide one delivering fluid system for a plurality of reagents. In this construction, one end of the fluid system is connected to a vessel containing a reagent, whereas the other end of the fluid system is connected to a vessel containing a sample. In addition, to the fluid system is connected one pump through a changeover valve, whereby the changeover valve is operative to suck the reagent, sample and simultaneously deliver both the sample and the reagent into a reaction vessel. In such well known apparatus, the fluid system is completely filled with the reagent, so that some reagent which has been sucked is not delivered and becomes useless. Moreover, the entire length of the flow path must be washed and cleaned whenever the kind of the reagent is changed. Furthermore, changeover mechanism and changeover operation of the valve is complex and hence the apparatus is not reliable in operation.

In a further well known apparatus described in Japanese Laid-Open and not examined Specification No. 5,790/79, reagent vessels are arranged on a turntable and the turntable is rotated in a given direction by a motor through a slip mechanism. When a vessel containing a desirous reagent arrives at a suction position, the turntable is electro-magnetically stopped so as to suck the reagent from the reagent vessel. The reagent vessels are preferably made small in size for the purpose of disposing them on the turntable. As a result, the reagent should be concentrated several tens times the concentration of the conventional reagent. Therefore, the reagent must be diluted by a diluent (for example, water) during the lapse of time from the step of sucking the reagent into the probe to the step of delivering the reagent into the reaction vessels. As a result, such means and step are necessarily added. Moreover, even when only one reagent is delivered, all the reagent vessels must always be rotated and stopped together with the turntable, so that a driving and stopping mechanism becomes necessarily large in size and complex in operation.

SUMMARY OF THE INVENTION

An object of the present invention, therefore, is to provide a delivering apparatus which can eliminate the above mentioned drawbacks, which can deliver a desired reagent or sample into a reaction vessel without moving a group of reagent or sample vessels and which is simple in construction and reliable in operation.

A feature of the invention is the provision in an apparatus comprising a delivering device including a probe and operative to suck at least one kind of liquids such as a plurality of reagents, samples or the like from respective vessels into the probe and deliver the liquid thus sucked from the probe into a reaction vessel, the improvement in which said probe is movable along a given moving path, said vessels containing said liquids to be delivered being provided with suction openings arranged at a plurality of fixed positions along the moving path of said probe, and in which said reaction vessel is movable along a path adjacent to and crossed with the moving path of said probe, and in which provision is made of means for locating said probe at any sucking position or at a delivering position with respect to said reaction vessel where said moving path of the probe is adjacent to or crossed with said moving path of the reaction vessel.

BRIEF DESCRIPTION OF THE DRAWINGS

The present invention will be described more in detail with reference to the accompanying drawings, in which.

DETAILED DESCRIPTION OF THE PREFERRED EMBODIMENTS

Figure 1:
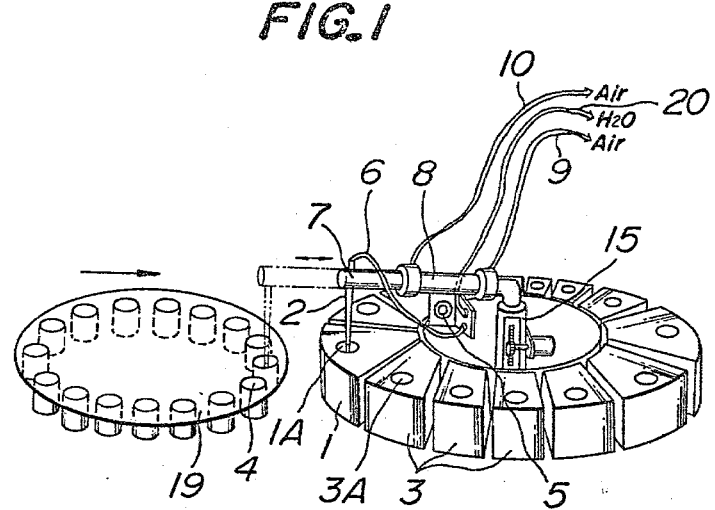
FIG. 1 is a perspective view of a first embodiment of a delivering apparatus according to the invention.
Figure 2:
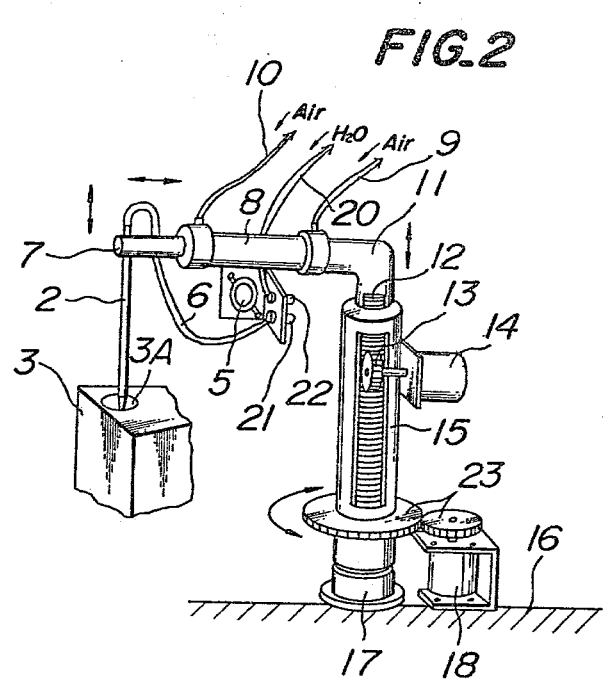
FIG. 2 is a perspective view showing essential parts of the embodiment shown in FIG. 1 in an enlarged scale.

FIGS. 1 and 2 show a first embodiment of an apparatus according to the invention. in FIGS. 1 and 2, reference numeral 1 designates a washing water vessel for washing and cleaning a probe 2. In order to prevent the probe 2 from being contaminated, it is desirous to always supply fresh washing water to the vessel 1 in a continuous manner. Reference numeral 3 designates a group of reagent vessels. In the present embodiment, openings 1A and 3A of the vessels 1 and 3 are located at positions below a circular moving path of the probe 2. The probe 2 can not only move along this circular path but also can move downward into the vessels 1, 3 through the openings 1A, 3A and upward from the vessels 1, 3. Moreover, the probe 2 can move forward and backward, i.e. can effect the reciprocal movement in the radial direction of the circular path. One end of the probe 2 is connected through a flexible tube 6 to a pump 5. The probe 2 is held by the front end of a piston 7 which is forward and backward movable by an air cylinder 8. It is preferable to provide a rotation preventive means (not shown) between the piston 7 and the cylinder 8. The piston 7 of the air cylinder 8 is made forward and backward movable by means of a change-over valve and pressure air supply source (not shown) such that when the piston 7 is forward moved the probe 2 is located at a position above a reaction vessel 4 and that when the piston 7 is backward moved the probe 2 is located at a position above the suction openings 1A and 3A of the vessels 1 and 3, respectively.

To that end of the cylinder 8 which is opposite to the piston 7 is connected an L-shaped shaft 11 provided with a rack 12. The rack 12 is meshed with a pinion 13 operative to be rotated by an electric motor 14 so as to move the probe 2 upward and downward together with the cylinder 8 and piston 7 by an electric signal supplied to the motor 14. The shaft 11 is inserted into a rotary cylinder 15 which is supported on a base 16 through a bearing 17. The cylinder 15 is rotated together with the shaft 11 by means of an electric motor 18, preferably a pulse motor which functions to determine an angular position through a pair of gears 19. If the cylinder 15 together with the shaft 11 are rotated, the probe 2 is also rotated by a required amount of angle along its circular moving path and is brought into a position above an opening of one of the reagent vessels 3 containing a reagent to be used.

The pump 5 connected to the probe 2 through the flexible tube 6 is operative to suck a required amount of reagent from the reagent vessel 3 into the probe 2 and discharge it from the probe 2 into one of the reaction vessels 4 arranged along a circular on a turntable 19 under control of external electric signals. This pump 5 should be advantageously compact in size and light in weight. For this purpose, use may be made of a pump having a diaphragm formed of piezoelectric material. This pump 5 is provided with two ports (not shown), one of which being connected to the probe 2 for sucking and discharging reagent and the other being connected to a tube 20. These ports are combined with two solenoid valves 21 and 22 which are operated under control of external control signals so as to enable a two-directional flow of liquid. If the solenoid valve 21 connected to the probe 2 is opened and the solenoid valve 22 connected to the tube 20 is closed, a positive voltage is applied to the diaphragm formed of piezoelectric material of the pump 5, to make the diaphragm concave in shape and to produce a negative pressure in the pump 5. As a result, a given amount of reagent is sucked from the reagent vessel 3 through the probe 2 into the pump 5. Then, if the solenoid valve 21 at the inlet side is closed and the solenoid valve 22 at the outlet side is opened, a negative voltage is applied to the diaphragm of the pump 5 to make the diaphragm convex in shape and produce a positive pressure in the pump 5. As a result, an amount of reagent in the pump 5 is discharged through the tube 20. If the tube 20 is connected to a water supply source (not shown) and the order of the opening and closing operations of the two solenoid valves 21 and 22 is made opposite to that of the above mentioned case, water is supplied from the source through the tube 20 into the pump 5 and then is discharged through the probe 2 into the reaction vessel 4. Therefore, the pump 5 may be used so as to deliver the reagent in the following two manners.

(1) The reagent is sucked from the inlet side and discharged from the outlet side into the reaction vessel 4.

In this case, the reagent passes the entire length of the flow path from the probe 2 through the pump 5 to the tube 20. As a result, if a plurality of reagents are delivered by means of one delivering apparatus, the entire length of the flow path must be washed and cleaned. Moreover, in addition to the amount of reagent to be delivered in practice, that amount of reagent which fulfills the entire length of the flow path must additionally be used, so that such additional amount of reagent becomes useless.

(2) The reagent is sucked from the inlet side of the pump 5 and is discharged also from the inlet side thereof.

In this case, as shown in FIG. 1, the required amount of the reagent only is sucked from the inlet side and only that amount of the reagent which has been sucked is discharged from the inlet side, so that the reagent is not used uneconomically. In addition, the flow path is not contaminated. In the embodiment shown in FIG. 1, the inlet side is able to be connected through the probe 2 to the washing water vessel 1. At first, water is repeatedly sucked into and discharged from the probe 2 by the pump 5 and the probe 2 is completely filled with water up to the front end thereof.

Thus, there is no air in the flow path when the reagent is sucked and discharged, so that it is possible to prevent the amount of delivering of reagent from becoming inaccurate due to the change in volume of air in a reliable manner. Moreover, cleaning of the flow path inclusive of the probe 2 can effectively be achieved by discharging the water from the flow path.

The operation of the above described apparatus as a whole will now be described.

In the first place, the probe 2 is positioned at the position above the washing water vessel 1. That is, the piston 7 is positioned at its rear position, the shaft 11 is positioned at its upper position and the rotary cylinder 15 is positioned at its angular position that the probe 2 is located at the position above the washing water vessel 1. Then, the motor 18 is energized to rotate the rotary cylinder 15 to move the probe 2 to the position above the opening 3A of the reagent vessel 3 which contains the reagent to be sucked and delivered. If the motor 18 is a pulse motor, the number of driving pulses corresponding to the angular positions of respective reagent vessels are set beforehand by means of a control unit (not shown). If the motor 18 is a d.c. motor or an a.c. motor, the rotary cylinder 15 is provided with an encoder which functions to count the number of output pulses, or a photosensitive switch or a microswitch or the like is provided at the position of each reagent vessel 3 so as to detect the position of the reagent vessel 3 and stop the motor 18 at a given angular position of the probe 2. Next, the motor 14 is energized to rotate the pinion 13 so as to descend the rack 12 of the shaft 11 and dip the probe 2 into the reagent in the reaction vessel 3. Under such condition, the pump 5 and the solenoid valves 21 and 22 are operated in the above described manner so as to suck a required amount of the reagent into the probe 2. Then, the motor 14 is rotated in an opposite direction to raise the probe 2 above the vessel 3. Then, the motor 18 is energized to rotate the rotary cylinder 15 to bring the probe 2 back to the position above the washing water vessel 1. At this angular position, the piston 7 is moved forward by the cylinder 8 to move the probe 2 to the position above the reaction vessel 4. Then, the pump 5 and the solenoid valves 21 and 22 are operated to discharge the reagent in the probe 2 into the reaction vessel 4. After the discharge of the reagent has been completed, the piston 7 is moved backward to its initial position so as to locate the probe 22 at the position above the washing water vessel 1. Then, the motor 14 is energized to descend the shaft 11 so as to dip the probe 2 into the washing water in the vessel 1, thereby cleaning the outer surface of the probe 2. At the same time, the pump 5 and the solenoid valves 21 and 22 are operated to discharge water in the flow path from the probe 2, thereby cleaning the inner surface of the probe 2. The washing water vessel 1 is always supplied with fresh water or the vessel 1 is made small in size such that when the water is discharged from the probe 2 into the vessel 1 the water is overflowed over the vessel 1. Thus, it is possible to simultaneously clean with water both the outer and inner surfaces of the probe 2.

Finally, the motor 14 is energized to raise the shaft 11 to bring back the probe 2 to the position above the washing water vessel 1, thereby completing one delivering step.

The turntable 1 is controled such that if the reaction vessel 4 is not located at the position corresponding to the position of the probe 2 located above the turntable 19, the turntable 19 is rotated by one step. Means for driving the turntable 19 may be provided with a position detector or a stopper, if necessary.

Figure 3:
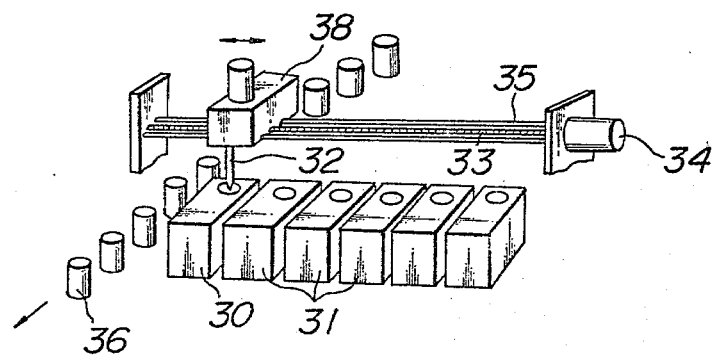
FIG. 3 is a perspective view of a second embodiment of a delivering apparatus according to the invention.
Figure 4:
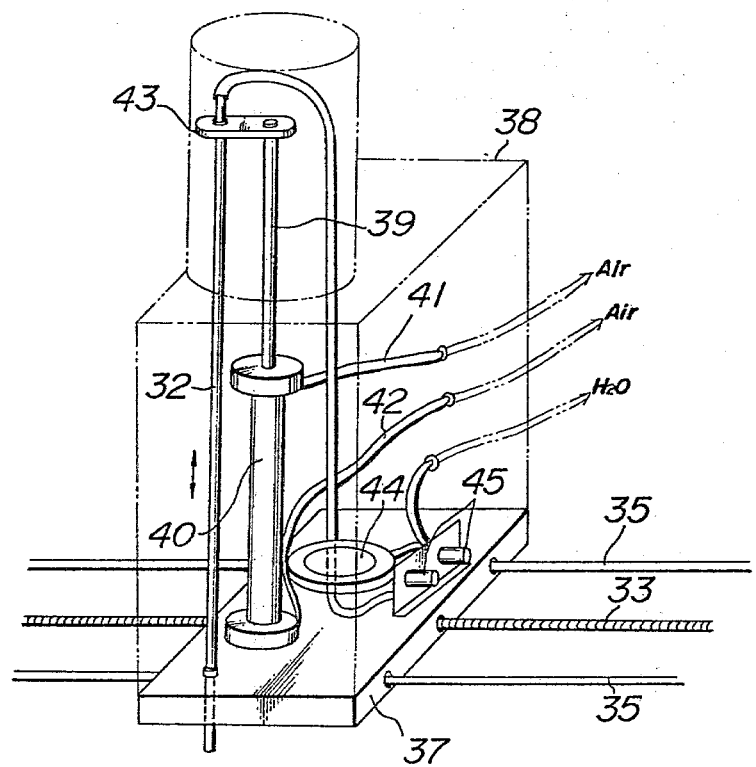
FIG. 4 is a perspective view of essential parts of the embodiment shown in FIG. 3 in an enlarged scale, a pump box being removed.

FIGS. 3 and 4 show a second embodiment of an apparatus according to the invention. In FIGS. 3 and 4, reference numeral 30 designates a washing water vessel and 31 a group of reagent vessels. Each of the vessels 30, 31 is provided with an opening arranged in line below a linear moving path of a probe 32. The probe 32 is made movable linearly along a linear moving path as well as movable upward and downward by a driving means to be described later. One end of the probe 32 is connected through a flexible tube to a pump. Reference numeral 34 designates a motor operative to move a pump box 38 linearly by means of guide rails 35 and a feed screw 33. If the motor 34 is a pulse motor, the number of pulses each corresponding to the position of the reaction vessel 36, the washing water vessel 30 and one of reagent vessels 31 is set beforehand in a control circuit of the motor 34. As a result, it is possible to locate the probe 32 at a desired position corresponding to an analytical item. If the motor 34 is a d.c. or a.c. motor, it is desirable to provide a position detector at each stop position of the motor 34 or the motor 34 is provided at its output shaft with an encoder so as to determine the position of the motor 34. The reaction vessels 36 are driven intermittently in synchronism with the delivering step by means of a drive means (not shown). Reference numeral 37 designates a slidable base of a pump box 38. The slidable base 37 is slidably engaged with the feed screw 33 so as to be reciprocated in the axial direction of the feed screw 33 when it is rotated. Reference numeral 39 designates a piston operative to be driven upward or downward by an air cylinder 40. To the upper end of the piston 39 is connected through a connector 43 the probe 32. Reference numeral 44 designates a diaphragm formed of piezoelectric material and 45 two solenoid valves. These members may be the same in construction as those described with reference to the first embodiment.

The operation of the second embodiment of an apparatus according to the invention will now be described. The probe 32 is filled with the washing water up to the front end thereof in the same manner as that effected in the first embodiment. In the initial condition, the pump box 38 is located at a position above the washing water vessel 30 and the probe 32 is located at its upper position. In the first place, the motor 34 is energized to rotate the feed screw 33 so as to move the slidable base 37, pump box 38 and probe 32 as a whole linearly to a position above a reagent vessel 31 containing a reagent to be sucked. Then, the cylinder 40 is operated to descend the probe 39 so as to dip the probe 32 into the reagent in the reagent vessel 31. Subsequently, the pump 44 and the solenoid valves 45 are operated to suck a required amount of reagent into the probe 32. Then, the cylinder 40 is operated to raise the piston 39 and hence the probe 32. Further, the motor 34 is energized to rotate the feed screw 33 so as to linearly displace the probe 32 to the position above the reaction vessel 36. At this position, the probe 32 may be descended into the reaction vessel 36, if necessary. The pump 44 and solenoid valves 45 are operated to suck and deliver reagent into the reaction vessel 36. Then, the motor 34 is energized to bring back the probe 32 to the position above the washing water vessel 30. At this position, the piston 39 is descended to dip the probe 32 into the washing water, thereby washing and cleaning the outer surface of the probe 32. Next, the pump 44 and the solenoid valves 45 are operated to discharge the water from the probe 32 so as to wash and clean the inner surface of the probe 32. Finally, the probe 32 is brought back to the position above the washing water vessel 30, thereby completing one delivering step.

Figure 5:
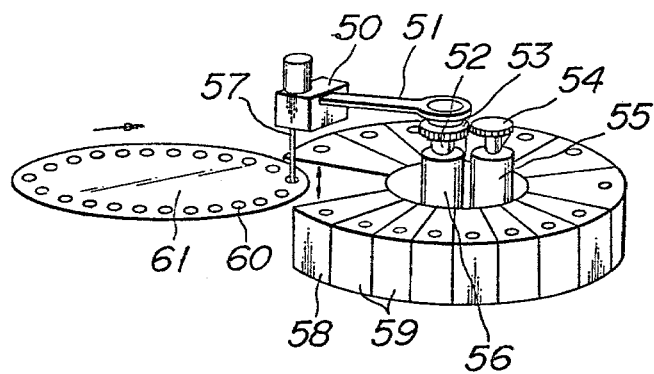
FIG. 5 is a perspective view of a third embodiment of a delivering apparatus according to the invention.
Figure 6:
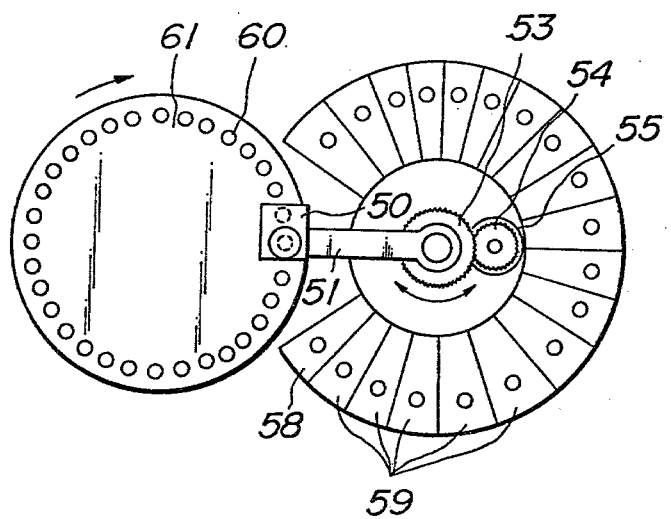
FIG. 6 is a plan view of the embodiment shown in FIG. 5.

FIGS. 5 and 6 show a third embodiment of an apparatus according to the invention. In FIGS. 5 and 6, reference numeral 50 designates a pump box connected to a rotary arm 51. The arm 51 is coupled with the shaft 52 provided with a gear 53 so as to move the pump box 50 to positions above respective suction openings of reagent vessels 59 and washing water vessel 56. The reaction vessels 60 are arranged along a circular moving path. The gear shaft 52 is jounaled in a bearing 56 and meshed with a gear 54 adapted to be rotated by a motor 55. To the pump box 50 is secured to a probe 57. Reference numeral 61 designates a turntable adapted to be driven intermittently in synchronism with the delivering step by means of a driving means (not shown). The turntable 61 is made circular in shape and the outer periphery thereof is brought into contact with the circular moving path of the probe 57. The reagent vessels arranged along the circular moving path of the probe 57 are not located near the turntable.

The operation of the third embodiment of the apparatus according to the invention will now be described. In the initial condition, the pump box 50 and the probe 57 are located at the position above the washing water vessel 58 and the probe 57 takes its upper position. Similar to the previous embodiments, the probe 57 is filled with water up to its front end. In the first place, the motor 55 is energized to move the probe 57 through the gears 53 and 54 and arm 51 to the position above a reagent vessel 59 containing a necessary reagent. Next, the probe 57 is descended and is dipped into the reagent so as to suck a required amount of reagent. Then, the probe 57 is raised and the motor 55 is energized to move the probes 57 to the position above the reaction vessel 60. At this position, the reagent is delivered into the reaction vessel 60, after which the probe 57 is moved to the position above the washing water vessel 58. Then, the probe 57 is descended and dipped into the washing water so as to wash and clean the outer surface of the probe 57. Moreover, water is discharged from the probe 57, thereby washing and cleaning the inner surface of the probe 57. Finally, the probe 57 is raised to complete one delivering step. The turntable 61 is fed step by step in synchronism with the delivering step.

Figure 7:
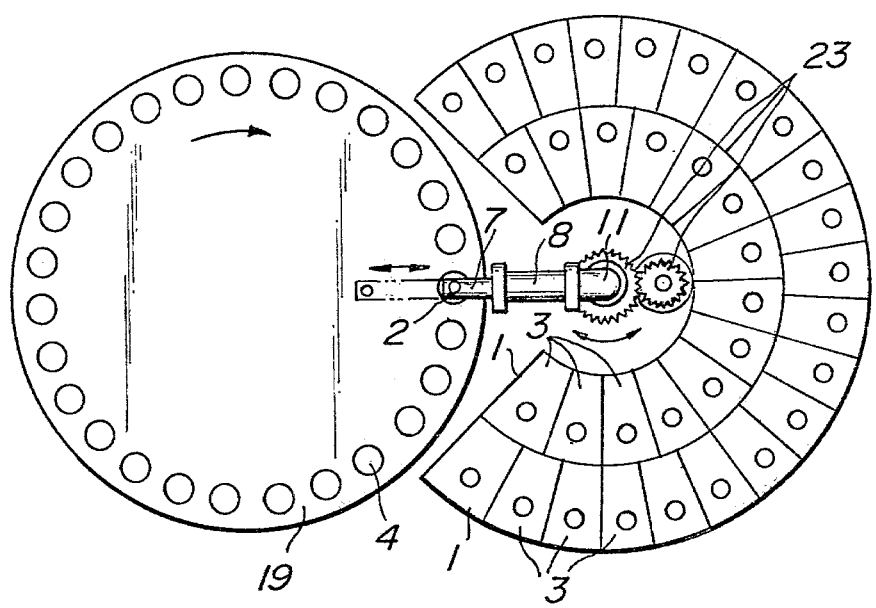
FIG. 7 is a plan view of a fourth embodiment of a delivering apparatus according to the invention.

FIG. 7 shows a fourth embodiment of an apparatus according to the invention. In the present embodiment, two rows of reagent vessels 3 inclusive of washing water vessel 1 shown in FIG. 1 are arranged concentrically about the center axis of the circular moving path of the probe 2 shown in FIG. 1. Provision is made of a mechanism for reciprocating and raising and lowering the probe 2 which is the same as that shown in FIG. 1. The present embodiment has the advantage that a number of different kinds of reagents can be used.

In the above described embodiments, the reagent is delivered from the reagent vessel into the reaction vessel. However, the reagent vessel may be replaced by a sample vessel. In this case, if the sample vessel with or without the reagent vessel is arranged along the probe moving path, it is possible to provide a sample delivering apparatus. If a large number of reagent vessels should be arranged, a plurality of rows of reagent vessels such as shown in FIG. 3 may be arranged in parallel and the position of the probe may be controlled in two directional manner as in the case of an X-Y plotter. In this case, it is preferable to provide a linear pulse motor and a driving mechanism operative to permit random access to any one of vessels.

The apparatus according to the invention provides the following advantages.

(1) The apparatus according to the invention is capable of using only one delivering apparatus for the purpose of delivering a plurality of liquids such as reagents, samples without moving the reagent vessels or sample vessels. That is, a large and complex driving mechanism required for the reagent turntable and moving the reagent vessels as a whole is not required, but only one delivering probe needs to be moved. Therefore, the apparatus according to the invention can be controlled in a rapid manner and is economical.

(2) The apparatus according to the invention is capable of using only one pump contrary to the conventional apparatus in which each reagent requires its own pump and hence is economical and reliable in operation.

(3) The apparatus according to the invention is not required to provide a complicate flow path changing over mechanism or a pump washing and cleaning mechanism as compared with the conventional apparatus which makes use of one reagent pump and flow paths of reagent sucking system are changed over. In addition, in the apparatus according to the invention, the flow path is not required to be filled with the reagent, so that the useless reagent can be omitted.

What is claimed is:

1. In an improved apparatus comprising a delivery device including a single probe and being operative to suck at least one kind of liquid such as a plurality of reagents, samples or the like, from respective vessels into the probe and deliver the liquid thus sucked from the same probe into reaction vessels, the improvement comprises: providing said probe to be movable along a given moving path, said vessels containing said liquids to be delivered being fixedly arranged at a plurality of predetermined sucking positions along the moving path of said probe and in which said reaction vessels are movable along a path which is crossed with the moving path of said probe at a discharging position, and in which provision is made of means for locating said probe at any sucking position to suck a given amount of liquid contained in the vessel situated at the relevant sucking position and then moving the probe into said discharging position to discharge the sucked liquid into a reaction vessel situated at the discharging position.

2. The apparatus according to claim 1, wherein along the moving path of said probe are arranged suction openings of washing water vessels for washing and cleaning said probe and said means for locating said probe at any suction position is operative to locate said probe at a washing water suction position thereof.

3. The apparatus according to claim 1, wherein provision is made of means for moving said probe along a circular or rectilinear moving path.

4. The apparatus according to claim 3, wherein said means for moving said probe along the circular moving path comprises a horizontal piston for holding said probe, a horizontal cylinder for forward and backward moving said piston together with said probe, and a vertical cylinder connected through an L-shaped shaft to said horizontal cylinder and operative to be upward and downward moved as well as to be rotated.

5. The apparatus according to claim 3, wherein said means for moving said probe along the circular moving path comprises a rotary arm connected at its front end to said probe and connected at its rear end to a driving mechanism for rotating said arm about a vertical axis.

6. The apparatus according to claim 3, wherein said means for moving said probe along the rectilinear moving path comprises a vertical piston for holding said probe, a vertical cylinder for upward and downward moving said piston together with said probe and connected to a slidable base, and a feed means including a feed screw threadedly engaged with said slidable base and operative to reciprocately move said slidable base together with said probe.

7. The apparatus according to claim 6, wherein a plurality of rows of reagent vessels are arranged in parallel and provision is made of means for controlling the position of the probe in X and Y directions.

8. The apparatus according to claim 4, wherein a plurality of rows of reagent vessels inclusive of washing water vessels are arranged concentrically about the center axis of said circular moving path of said probe.

* * * * *